US012648904B2

(12) United States Patent
Yang et al.

(10) Patent No.: US 12,648,904 B2
(45) Date of Patent: *Jun. 9, 2026

(54) POROUS NANOCOMPOSITE MEDICAL IMPLANT DEVICE

(71) Applicant: Lynthera Corporation, Lancaster, PA (US)

(72) Inventors: Arthur Jing-Min Yang, Bethesda, MD (US); Naiping Hu, Cincinnati, OH (US); Roman C. Domszy, Lancaster, PA (US); Cesar Torres Luna, College Park, MD (US); Jeffry C. Yang, Bethesda, MD (US)

(73) Assignee: Lynthera Corporation, Lancaster, PA (US)

( * ) Notice: Subject to any disclaimer, the term of this patent is extended or adjusted under 35 U.S.C. 154(b) by 819 days.

This patent is subject to a terminal disclaimer.

(21) Appl. No.: 17/996,124

(22) PCT Filed: Apr. 14, 2021

(86) PCT No.: PCT/US2021/027215

§ 371 (c)(1),
(2) Date: Oct. 13, 2022

(87) PCT Pub. No.: WO2021/211670

PCT Pub. Date: Oct. 21, 2021

(65) Prior Publication Data

US 2023/0190644 A1 Jun. 22, 2023

Related U.S. Application Data

(60) Provisional application No. 63/010,351, filed on Apr. 15, 2020.

(51) Int. Cl.
| | |
|---|---|
| *A61K 9/00* | (2006.01) |
| *A61L 27/48* | (2006.01) |
| *A61L 27/54* | (2006.01) |
| *A61L 27/56* | (2006.01) |

(52) U.S. Cl.
CPC ............ *A61K 9/0051* (2013.01); *A61L 27/48* (2013.01); *A61L 27/54* (2013.01); *A61L 27/56* (2013.01); *A61L 2400/12* (2013.01)

(58) Field of Classification Search
None
See application file for complete search history.

(56) References Cited

U.S. PATENT DOCUMENTS

| | | | | |
|---|---|---|---|---|
| 11,504,323 B2 * | 11/2022 | Yang | .................... | A61K 31/196 |
| 2013/0006172 A1 | 1/2013 | Desai | | |
| 2019/0224045 A1 * | 7/2019 | Yang | .................. | A61K 31/5575 |
| 2020/0206030 A1 | 7/2020 | Yang et al. | | |

FOREIGN PATENT DOCUMENTS

WO      2020056467 A1      3/2020

OTHER PUBLICATIONS

Cesar Torres-Luna et al.: "Extended delivery of non-steroidal anti-inflammatory drugs through contact lenses loaded with Vitamin E and cationic surfactants", Contact Lens and Anterior Eye, vol. 42, No. 5, Oct. 1, 2019, pp. 546-552.
International Search Report dated Jul. 8, 2021 cited in PCT/US2021/027215, 3 pages.

* cited by examiner

*Primary Examiner* — Carlos A Azpuru
*Assistant Examiner* — Casey S Hagopian
(74) *Attorney, Agent, or Firm* — Perkins Coie LLP; Viola Kung

(57) ABSTRACT

The present invention relates to a drug-eluting nanoengineered medical implant/contact device. The device comprises a nanocomposite and a drug, wherein the nanocomposite comprises hydrophilic polymer domains, hydrophobic polymer domains, water pores, and boundary charged double layers; wherein when the drug is hydrophilic, at least 80% of the drug partitions in the boundary charged double layers formed at the boundary interface of the hydrophilic polymer domains and water pores, and when the drug is hydrophobic, at least 80% of the dmg partitions in the boundary charged double layers formed at the boundary interface of the hydrophobic polymer domains and water pores. The device is configured to sustain the release of the drug at high precision and long duration.

19 Claims, 12 Drawing Sheets

POROUS NANOCOMPOSITE MEDICAL IMPLANT DEVICE

This application is a National Stage of International Application PCT/US2021/027215, filed Apr. 14, 2021, which claims the benefit of priority to U.S. Provisional Application No. 63/010,351, filed Apr. 15, 2020. The contents of the above-identified applications are incorporated herein by reference in their entireties.

FIELD OF THE INVENTION

The present invention relates to a drug-eluting nanoengineered medical implant/contact device (NMID) comprising an active pharmaceutical (a drug or growth ingredient), aqueous pores, one or more hydrophilic domains, one or more hydrophobic domains, and boundary charged double layers; the device is configured to sustain the release of the pharmaceutical at high precision and long duration (more than a week). This disclosure describes the preparation of a porous nanocomposite with adequate water affinity, ion permeability and gas to permeability as well as a method of utilizing the electrostatic forces of charges implanted on the pore-polymer interfaces (interphase Charges Layer) to enhance the partition and retention of an oppositely charged pharmaceutical in an engineered device delivery. The NMID is to be utilized for the controlled delivery of active pharmaceutical and other functional ingredients to a body part in vivo.

BACKGROUND OF INVENTION

The technology of designing and making a medical implant has progressed over three generations starting from the primitive state of just using inert materials, through the second level of resolving body's immune resistance (often done by incorporating a biocompatible surface coating such as PEG), and now arrived at a sophisticated stage of implementing favorable interactions with a body system not just to heal the impaired, but also facilitate body's full regeneration. The newest biomedical devices are to be purposefully engineered to pharmacologically intervene a host body function by delivering pre-embedded functional pharmaceutical ingredients including, but not limited to, essential building blocks, nutrients, genes, growth factors, signaling peptides, and/or stem cells to stimulate and accelerate the desired cell responses, healing and regeneration reactions.

A core technology of the new biomedical devices is to nanoengineer a composite material either for formulating the device body or its exterior coating for facilitating a sustainable delivery of one or multiple drugs with a high-precision dosage, at a near constant rate, and of extended duration. The recent progress in contact lens material technology has provided a platform for the further advancement of this core technology. The silicone-hydrogel composite technology, since its implementation in 1997, has improved both the water affinity and oxygen permeability of a contact lens and transformed it into a breathable and hydrophilic soft tissue-resembling device.

U.S. Pat. No. 10,617,559 discloses a device comprising: (i) at least a drug, (ii) one or more reservoir domains, and (iii) a barrier domain of layer configuration (or a barrier layer) to block the drug diffusion paths from the reservoir domain to the ocular surface in the eye of the subject.

Prior arts indicated that there are three transport modes of a drug's permeation through a porous composite. These results had shown that, after immersing a lens into a tear sink, a burst release from the dissolved drugs in aqueous pores occurred within a few hours. The second mode of release, primarily from drugs adsorbed at the domain-pore interfaces, lasted for more than a day. The drugs entrapped within the solid polymeric domain came out to the slowest and the timing could be sustained for many weeks depending on the solid polymer's relaxation time scale (related to the polymer's glass transition temperature). Many efforts have focused on extending the majority (80%) of drug release to more than a week, including the use of a barrier coati rig, a dissolved diffusion barrier, or charged surfactants.

There exists a need for a drug-eluting medical implant/contact device that is safe and provides a sustained release of the drug.

DETAILED DESCRIPTION OF THE INVENTION

Definitions

Figure 1:
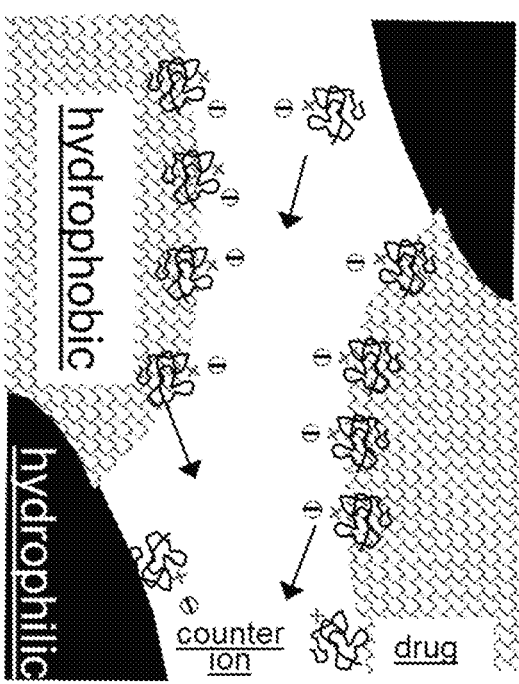
FIG. 1. Drug permeation through a porous nanocomposite

A "medical implant/contact device" as used herein, refers to a device that is either in contact with a body part, or being implanted within a body environment to intervene a specific body function, or condition, Examples are, but not limited to, a surgically implanted body part, a stent, a chemo port, a scaffold for tissue growth, a contact lens, a tooth implant, a skin pad, a wound-healing bandage, etc.

A "drug" or "pharmaceutical compound" as used herein, refers to a molecule having an activity to cause a physiological change in a subject, such as a pharmaceutical drug or a nutrient.

A "charged drug or pharmaceutical compound" means their molecules are either cationic or anionic under the normal physiological conditions. They can be among the class of compounds having a pKa, pKb, or an isoelectric point, which include, but not limited to, proteins, small peptides, molecules with other Lewis acid or base groups.

A "hydrophobic/hydrophilic" ratio is a measure of a material's hydrophobicity based on its solubility and partition between hydrophobic octanol and hydrophilic water. It is normally referred to a material constant logP of octanol/water, where P is a partition coefficient ratio of a soluble component between octanol and water (Sangster J, J Phys Chem Ref Data 1989; 18: No. 3). A high logP value means hydrophobic and a low or negative value means hydrophilic.

A "junction potential" is a Coulomb potential resulted from the diffusion of electrons or ions at the boundary of a conductor, semiconductor, or electrolyte solution. Examples are metal couple j unction, P-N junction, liquid junction, or cell aqueous medium junction.

A "boundary charged double layer", as used herein in the present device, consists of a negatively-charged layer and a positively-charged layer, and is formed at the boundary interface of the hydrophilic/hydrophobic polymer domains and water pores. The boundary charge double layer often consists a surface Stern layer and a diffusive Debye layer like those of a colloidal particle or an ionic crystal. For example, the boundary charged double layer is formed from the charge of a head group of a boundary charge modifier, and (ii) the charge of the drug or a counter ion to the charged head group.

A "boundary charge modifier" is a compound implanted onto a water-solid interface, either by physical dissolving or chemical bonding, to create a boundary charged double layer on the water-solid interface and a junction potential through interfacial ion dissociation or exchange in an aqueous medium.

A "good solvent" to a polymer is a solvent whose molecules have an energetically favorable interaction with the monomer segments so that their solvation effect in the polymer causes the polymer coils to expand and their infiltration leads to polymer swelling.

Porous Nanocomposite for Drug Delivery

The inventors have discovered a new generation of nano-engineered contact/implant biomedical devices that have the following favorable functions: (a) Compatible to and permeable by a body fluid, (b) Efficient exchange of oxygen and carbon dioxide, (c) Strong adhesion (hydrophobic bonding) of cells to the hydrophobic domains, (d) Extendable drug releasing rate through composite material engineering.

The present invention provides a medical device comprising a drug and a nanocomposite. In a first aspect, the medical device comprises hydrophilic polymer domains, hydrophobic polymer domains, water pores and charged double layers; wherein when the drug is hydrophilic, at least 80% of the drug partitions in the charged double layers formed at the interphase of the hydrophilic polymer domains and water pores, and when the drug is hydrophobic, at least 80% of the drug partitions in the charged double layers formed at the interphase of the hydrophobic polymer domains and water pores.

In a second aspect, the medical device comprises hydrophilic polymer domains, water pores and charged double layers; wherein at least 80% of the drug partitions in the charged double layers formed at the interphase of the hydrophilic polymer domains and water pores.

In the present device, each of the boundary charged double layers is formed from (i) the charge of a head group of a boundary charge modifier, and (ii) the charge of the drug or a counter ion to the charged head group, wherein the boundary charge modifier is a molecule having a charged head group and a hydrophobic tail and is immobilized at the boundary charged double layer throughout the use life of the device.

The present invention also provides a method for making such a device.

This disclosure provides a design of the device composite consisting pores of water, hydrophilic polymer domains (monomer logP<1), and hydrophobic polymer (monomer logP>3) domains among which the aqueous pores and the hydrophilic polymer can facilitate wetting by a body fluid (for examples, tear or blood) while the hydrophobic domains enhance gas (for example, oxygen, or carbon dioxide) permeation as well as the adhesion of hydrophobics (for examples, cells or proteins). The pore and domain sizes are controlled to be at nanometer scale to increase the pore-surface area and device interfacial interactions. A variety of hydrophilic and hydrophobic polymeric materials can be used for the present invention.

This disclosure also outlines the composition design of NMID for the loading and delivery of a pharmaceutical active ingredient with using one component domain with a high drug affinity as its reservoir while utilizing the other domain (with much lower drug solubility) as a barrier to regulate the drug's releasing rate into a body fluid, The water content is adjustable for further regulating the overall drug delivery rate.

This disclosure finally provides a method to utilize engineering domain morphologies (for example, size, geometry and surface area) along with incorporation of boundary charge modifier(s) at polymer-aqueous pore interfaces to significantly enhance or reduce the releasing of a charged pharmaceutical.

A porous nanocomposite of the present invention can be further bioengineered for a variety of in-contact or in-situ medical devices including, but not limited to, drug delivery matrixes, implant devices, tissue engineering scaffolds, chemo port, wound dressing patches, cosmetic masks, etc. The following sections show how inventors ¯tailor a porous nanocomposite to make a device respectively achieving (a) high compatibility to and permeability by a body fluid, (b) efficient exchange of oxygen and carbon dioxide, (c) strong adhesion (hydrophobic bonding) of cells to the hydrophobic domains, (d) extendable drug releasing rate through composite material engineering.

In one embodiment, the porous nanocomposite is composed of water pores (10-80% or 10-40% by weight), hydrophilic polymer domains made (10-50% by weight) from hydrophilic monomers of I ogP in the range of -1 to 1, hydrophobic polymer domains (10-50% by weight) made from hydrophobic monomers with a logP>3, and physically or chemically incorporated boundary charged double layers (1-20% or 1-10% by weight). In another embodiment, the porous nanocomposite is composed of water pores (10-80% or 10-40% by weight), hydrophilic polymer domains made (10-90% by weight) from hydrophilic monomers of logP in the range of −1 to 1, and physically or chemically incorporated boundary charged double layers (1-20% or 1-10% by weight).

The composition and morphological feature (for examples, the hydrophobic/hydrophilic ratio, domain size shape, and orientation) are tailored in each application based on the required, or desired specifications of the body fluid wetting, oxygen exchange rate, cell adhesions as well as growth.

A Porous Nanocomposite Compatible to Body Fluid, Permeable to Oxygen, $CO_2$, and/or Superior in Facilitating Cell Adhesion/Growth In one embodiment, the hydrophilic domain component of the composite is elected from any of the hydrophilic components listed in Table 1A, 1B, 1C to raise the device's water affinity, and the hydrophobic domain component is selected from any of the hydrophobic components listed in Table 1A, 1B, or 1C to enhance the device's oxygen permeability (Dk≥100) four to five times higher than pure hydrogel device (Dk~20). A nanocomposite contact lens can be made from these acrylic oligomers, or prepolymers by a thermal curing (100° C.-120° C.) process. The porosity (for example, 30-40% by volume) is created by a to solvent/cosolvent system used for uniformly mixing the two different types of polymer, followed by washing/solvent exchange process to infuse water into pores. The hydrogd and aqueous pores allow easy permeation of body fluid while the flexible, less cohesive hydrophobic polymers is highly permeable to gases.

TABLE 1A

Common materials used to make hydrogel soft contact lens

| Hydrophilic component | Hydrophobic component |
|---|---|
| 2-Hydroxyethyl methacrylate ("HEMA") | Methyl methacrylate ("MMA") |
| N,N-dimethylacrylamide ("DMA") | |

6

TABLE 1A-continued

Common materials used to make hydrogel soft contact lens

| Hydrophilic component | Hydrophobic component |
|---|---|
| N-vinyl-2-pyrrolidone ("NVP") | Isobutyl methacrylate |
| 4,4-Dimethyl-2-vinyl-2-oxazolin-5-one | Pentyl methacrylate |
| Methacrylic acid ("MAA") | Cyclohexyl methacrylate |
| N-(Hydroxymethyl)acrylamide | Lauryl methacrylate |
| N-[3-(Dimethylamino)propyl]methacrylamide | |
| Ethylene glycol dimethacrylate | |

TABLE 1B

Common materials used to make silicone-hydrogel soft contact lens

| Hydrophilic component | Hydrophobic component |
|---|---|
| 2-Hydroxyethyl methacrylate | 3-[Tris(trimethylsiloxy)silyl]propyl methacrylate ("TRIS") |
| N,N-dimethylacrylamide | |
| N-vinyl-2-pyrrolidone | 3-Methacryloxy-2-hydroxy-propoxy(propylbis(trimethylsilyloxy)methylsilane ("SIGMA") |
| 4,4-Dimethyl-2-vinyl-2-oxazolin-5-one | |
| Methacrylic acid | Fluorosiloxane macromer |
| 2-(Methacryloyloxyethyl)-2-(trimethylammonioethyl) phosphate | Mono-(3-methacryloxy-2-hydroxypropyloxy)propyl terminated, mono-butyl terminated polydimethylsiloxane |
| Ethylene glycol dimethacrylate | |
| Poly(N-vinyl pyrrolidone) ("PVP") | Mono-methacryloxypropyl terminated polydimethylsiloxane |
| Triethyleneglycol dimethacrylate | |

Table 1C shows principle monomers of some commercial contact lenses. Tale 1C is from "Dynamic Contact Angle Analysis of Silicone Hydrogel Contact Lenses", Michael Leonard Read, Philip Bruce Morgan, Jeremiah Michael Kelly And Carole Maldonado-Codina, J Biomater Appl published online 10 Mar. 2010). The following additional abbreviations are used in Table 1C. mPDMS: monofunctional methacryloxypropyl terminated polydimethylsiloxane; EGDMA: ethyleneglycol dimethacrylate; TEGDMA: tetraethyleneg,lycol dimethacrylate; TPVC: tris-(trimethyl siloxysilyl) propylvinyl carbamate; NVA: N-vinyl amino acid; PBVC: poly (ditnethysiloxy) di (silybutanol) bis (vinyl carbamate); M3U: αω-bis(methacryloyloxyethyl iminocarboxy ethyloxpropyl)-poly(dimethylsiloxane)-poly(trifluoropropylmethylsiloxane)-poly(methoxy-poly(ethyleneglycol)propylmethyl-siloxane; FMM: α-methacryloyloxyethyl iminocarboxyethyloxypropyl-poly (dimethylsiloxy)-butyldimethylsilane; TAIC: 1, 3, 5-triallyl-1, 3, 5-ttiazine-2, 4, 6(1H, 3H, 5H)-trione; IBM: isobornyl methacrylate; HOB: 2-hydroxybutyl methacrylate; NMNVA: N-methyl-N-vinyl acetamide; AOE: 2-allyloxy-ethanol.

TABLE 1C

Commercial Contact Lens

| Lens type | Brand name | Manufacturer | Principal monomers | Water content (%) | Modulus (MPa) | Surface treatment |
|---|---|---|---|---|---|---|
| Asmofilcon A | PremiO | Menicon | Silicone methacrylates, silicone acrylates, DMA, Pyrrolidone derivative | 40 | 0.91 | Plasma coating and plasma oxidation |
| Balafilcon A | Purevision | Bausch & Lomb | NVP, TPVC, NVA, PBVC | 33 | 1.06 | Plasma oxidation |
| Clariti | Clariti | Sauflon | Alkyl methacrylates, silicone acrylates, siloxane monomers, NVP | 58 | 0.50 | None (inherently wettable) |

TABLE 1C-continued

Commercial Contact Lens

| Lens type | Brand name | Manufacturer | Principal monomers | Water content (%) | Modulus (MPa) | Surface treatment |
|---|---|---|---|---|---|---|
| Comfilcon A | Biofinity | CooperVision | M3U, FMM, TAIC, IBM, NMNVA NVP, HOB | 48 | 0.75 | None (inherently wettable) |
| Enfilcon A | Avaira | CooperVision | M3U, TEGMA, MMA NMNVA, AOE | 46 | 0.50 | None (inherently wettable) |
| Galyfilcon A | Acuvue Advance | Johnson & Johnson | mPDMS, DMA, HEMA, SiGMA TEGDMA, PVP | 47 | 0.43 | None (internal wetting agent, PVP) |
| Lotrafilcon A | Air Optix Night and Day | CIBA Vision | DMA, TRIS, fluorine-containing siloxane macromer | 24 | 1.50 | Plasma coating |
| Lotrafilcon B | Air Optix | CIBA Vision | DMA, TRIS, fluorine-containing siloxane macromer | 33 | 1.22 | Plasma coating |
| Narafilcon A | 1-Day Acuvue TruEye | Johnson & Johnson | Hydroxy-functionalized mPDMS, DMA, HEMA, TEGDMA, PVP | 46 | 0.66 | None (internal wetting agent, PVP) |
| Senofilcon A | Acuvue Oasys | Johnson & Johnson | mPDMS, DMA, HEMA, SiGMA, TEGDMA, PVP | 38 | 0.72 | None (internal wetting agent, PVP) |
| Silfilcon A | Air Optix Individual | CIBA Vision | DMA, TRIS, fluorine-containing siloxane macromer, styrene | 32 | 1.10 | Plasma coating |

In one embodiment, the hydrophilic component can be selected from a monomer, oligomer, or prepolymer that contains at least one hydrophilic group of hydroxyls, alkyl glycol, amine, lactam, carboxylic, or sulfonic group. The hydrophobic component can be composed of monomer groups with a logP>3. These non-compatible components can be either premixed within a compatible solvent/cosolvent system, or to be pre-reacted into block copolymers before being finally cured into a uniform nanocomposite.

In one embodiment, the hydrophilic polymer domains are made ten times smaller than the hydrophobic domain average size so that the hydrophobic domains are completely immersed into a continuum mixture of hydrophilic domains and aqueous water. This to morphology, hydrophobic domain immersed in a hydrophilic continuum enhances the composite's water affinity, contact angle and capillary infiltration.

In one embodiment, the hydrophobic domains are in an elongated needle shape, or part of an interpenetrating network with the hydrophilic phase, to enhance Dk of oxygen permeability to above 100.

In another embodiment, the device surface comprises hydrophobic domains of the size a fraction of a cell, (for example, domain size between 10 nm to 1 micron or 10-100 nm) and surrounded by hydrophilic domains and water pores of even a smaller size (for example, ten times smaller than the size of the immersed hydrophobic domain) to allow enhanced cell adhesion to the device surface via hydrophobic bonding (enhanced aggregation in aqueous environment).

Composite Domain Morphology for Controlling Drug Delivery Rate

The present invention transports an active functional ingredient to a host body environment through a porous nanocomposite with engineered precision and rate. In this disclosure, we explore the transferring of an active ingredient (a drug) in such a composite with using one type domains having a high drug affinity as its reservoir while utilizing the other domains (with substantially lower drug solubility) as a barrier to regulate drug releasing rate. Drug passing through the connecting nanopores within such a dual-domain composite resembles the molecular elution in a chromatography column of which the drug retention time can be precisely regulated by its attraction to the affinity column components.

Figure 2:
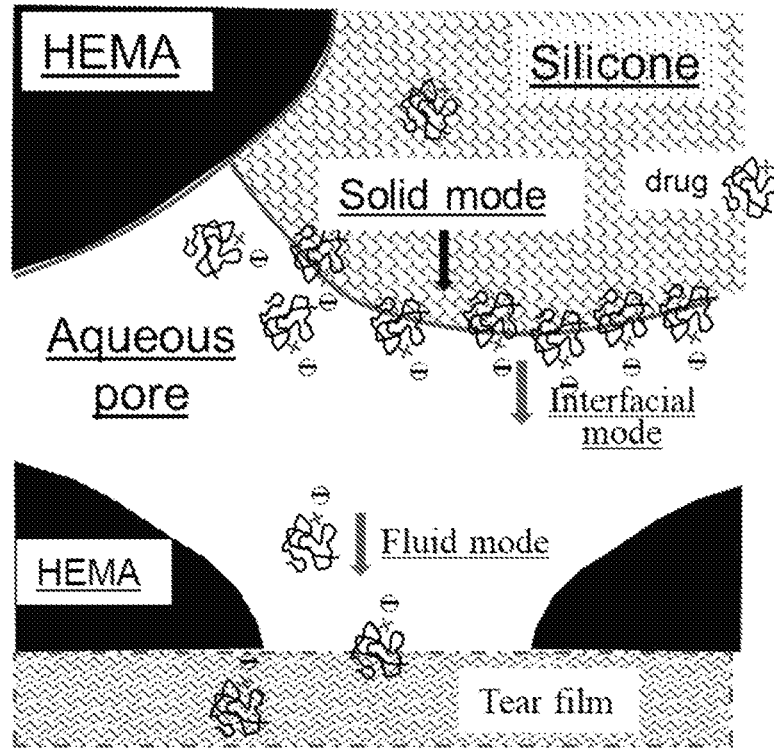
FIG. 2. Three modes of drug transport through a porous nanocomposite

Drug transport through (or release from) a porous hydrophobic-hydrophilic composite can be best modeled by first studying its permeation within each individual component, followed by an effective average over the whole composite (i.e. to apply the effective medium theory of transport coefficients, reference "Effective Medium Theory, Principles and Applications", Second Edition, Tuck C. Choy, Oxford University Press, 2016) Drug permeation rate in each domain is generally governed by the multiplication of the drug's solubility (S) and diffusivity (D) in the domain, i.e. Permeability =S×D. In the composite of interest, the aqueous phase in the pore often has the highest diffusion constant (normally several orders of magnitude higher) than the other two polymeric domains, but it does not necessarily mean its permeation constant is the highest due to a possible low aqueous solubility of a drug. Many drugs with an appreciable hydrophobic segment may have the highest drug permeation rate at an interfacial zone due to the higher affinity to an interfacing hydrophobic domain combined with high diffusion speed in the surrounding aqueous medium. FIG. 1 illustrates that a drug with a charge head group and a hydrophobic tail strongly adheres to the hydrophobic polymer pore surface and therefore can have a high partition and permeation constant at the interfacial zone due to the enhanced affinity. A drug is discharged from a porous nanocomposite by three modes, fluid mode through pore water (fastest), interfacial mode through solid boundary layer then the water pores (medium speed), and solid mode through a bulk polymer. FIG. 2 illustrates that although the diffusion through the pore fluid is normally the fasted mode of transport, the substantially higher partition of a charged hydrophobic drug at the interface can make the interfacial drug release the most dominant mode, especially when the interfaces are attached with the oppositely charged modifiers such as oleic acid.

Our modeling results, confirmed by examples disclosed, have shown that the most effective way of controlling drug deliveries through a porous nanocomposite is by raising the drug's partition coefficient and consequently its loading population at the polymer-pore interfacial zone. Our innovation strategy is to make the drug's interfacial releases the most dominant mode (over 80% of the total capacity) by incorporating boundary charge modifier(s) at polymer-water interfaces to substantially increasing a drug's partition coefficient in the boundary layer over those in the pore water or solid polymers. The present invention enhances drug delivery from the interfacial zone in a porous nanocomposite.

The interfacial area of a porous composite can be proportionally increased to above 100 m²/grain by lowering the solid domain size down to nanometer scales. This invention discloses that a porous nanopore composite, with such a high pore surface area, can be further prepared by planting a boundary charge double layer, either by solvent loading or chemical addition of a boundary charge modifier, at polymer-water interfaces in the nanocomposite. The boundary charge migration can generate a Coulomb junction potential at the modified aqueous interfaces so that the strong electrostatic attraction between the boundary charges and an oppositely charged pharmaceutical enhance the partition, population and retention of the drug. As shown by examples in the experimental section, such a nanoengineered device, having long-range ($1/r^2$) electrostatic forces between the drug molecules and interfacial charges at the boundary zone as well as throughout the whole nano-scaled pores, enables one of the most effective mechanisms in controlling the precision and duration of drug delivery through a nanopore composite. In one embodiment, the anionic charges of surface implanted oleic acid extended the release of catioic bupivacaine hydrochloride (BUP) by 50 fold. In another embodiment the extension is by 60 fold. (Examples in FIGS. 7 & 8)

Composite Morphology to Facilitate Controlling of Drug Delivery

Either the hydrophilic polymer (logP<1) or the hydrophobic polymer (logP>3) phases can be selected as a drug reservoir phase based on matching with the logP of the drug's hydrophobic segment. The domain size of the drug reservoir polymer is preferred to be in nanometer scale (10-100 nm) to maximize the domain-pore interface area and drug partition.

Utilizing Electrostatic Interactions at Reservoir-Pore Interfaces to Retain Charged Drugs Any compound with an end group that can exchange ions (including hydronium ion $H_3O^+$) in aqueous medium can be used as a Boundary Charge Modifier. A compound with a pKa, Pkb, isoelectric point, and dissociable ions (for examples, alkaline, halide, quaternary ammonium, etc.) can be implanted onto a polymer-water boundary to create charge layers by, ionic dissociation or hydronium adsorption. Polymer boundary modification can be accomplished by chemically reacting with a charge modifier (for example, a reactive acrylic acid, amine, or imine moiety). Or a boundary charge modifier with a segment of high affinity to the polymer can be physically implanted by a polymer solvation process as disclosed below. Such molecules are most stable with the hydrophobic tail residing in the high-affinity polymer reservoir and the charged head group all immersed into the aqueous phase and surrounded by water molecules as well as counter ions. In the device of the present invention, the boundary charge modifiers and the charged drug form charged double layers at the interface of the water pores and hydrophobic/hydrophilic polymer.

Based on our modeling and experimental results, we set a general guideline for choosing an appropriate boundary charge modifier (BCM) for each medical implant/conta.ct device in the extended delivery (more than a week) of charged drugs, namely; (1) The aqueous solubility of the physically implanted BCM must be low to minimize its leaching during a device's storage time or in an extended drug delivery period. (2) The BCM preferably to be neutral in physiological pH to avoid unintended electrostatic interactions with host body cells or other functional ingredients external after leaching from a device; (3) The BCM is preferably to be metabolically inert, or friendly, to minimize impacts from an accidental discharge, or its accumulation after long-time use.

From the above assessments, we choose to use long chain ($C_{8-24}$) fatty acids as an anionic BCM in long-term release of cationic pharmaceuticals from a porous nanocomposite medical implant/contact device. Organic fatty acids are biocompatible as well as generally being of low toxicity. in fact, some omega-3 fatty acids, for example of alpha-linolenic acid (ALA), eicosatetraenoic acid (EPA), and docosahexaenoic acid (DHA) have important health benefits. Nevertheless, our intent in using these compounds is to control the delivery of oppositely charged drugs and our protocol of loading them into porous nanocomposite is designed to minimize their discharge in vivo.

For anionic pharmaceuticals we need to incorporate an insoluble and biofriendly cationic BCM into pore surface of the nanocomposite. in one embodiment we selected sphingosine to extend the release DFNa. Sphingosine has a similar structure to oleic acid with a primary amine head instead of carboxylic acid. It is nontoxic and a metabolic byproduct.

While all these compounds are common surfactants for oil-water interfaces, their use as boundary charge modifiers to create boundary charged double layers in the medical device of the present invention require special processing schemes as discovered by the inventors, due to their inherent limitation of low solubility in the polymer and low critical micelle concentrations to form micelles in water.

Common oil-water surfactants such as fatty acids or alkyl amines are not a natural surfactant to polymers. The inventors have discovered that their population density at the water-polymer boundary (different from that at a water-oil boundary) can be enhanced by a physical implantation, or chemical reaction in order to proportionally increase their subsequent charge interactions with a charged drug. A physical implantation method is disclosed in one embodiment in next sections. A boundary charge modifier is physically carried into the polymer by infiltration and the surface loading density is proportionally increased by the solvent swelling of host polymer.

Increasing Drug Loading (Partition) at Pore Interfaces by Charge Interaction

By reducing drug reservoir domain size to nanometer scale, we substantially increase the interfacial area and the drug population therein proportionally. With the incorporation of charge double layer at the polymer-pore interfaces we substantially lower the drug chemical potential ($\mu_i = \mu_i + zF\phi$) by creating an oppositely charged interface and thus, raise the drug partition and loading in the interfacial zone.

Figure 3:
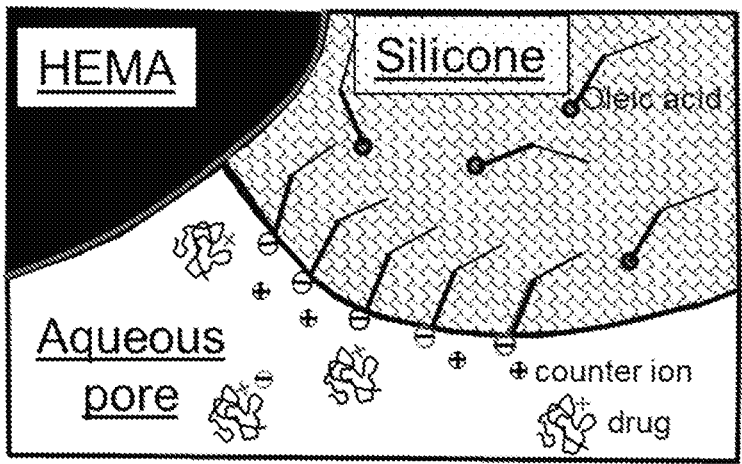
FIG. 3. The dissociation of oleic acid molecules at pore-domain interface enhances a cationic drug's partition and retention FIG. 4. Correlation of oleic acid loading and concentration of soaking solutions for two different silicone hydrogel commercial lenses: ACUVUE TruEye® and ACUVUE Oasys®. The R2 of the fitted linear lines are 0.996 (TruEye®) and 0.998 (Oasys®). Data are presented as mean +/− standard deviation with n=3.

Creating Charge Double Layer on Interfaces of Aqueous Pore and Hydrophobic Polymer The present invention further provides a method to load a water-insoluble fatty acid directly to polymer domains using a good solvent of the polymer which also has a higher solubility of fatty acid than water. A "good solvent" to a polymer is a solvent whose molecules have an energetically favorable interaction with the monomer segments so that their solvation effect in the polymer causes the polymer coils to expand and their infiltration leads to polymer swelling. The loading solvent is preferably to be a good solvent to the polymer so that the drug loading can be accelerated and even supersaturated with the solvent swelling the polymer. Such a good solvent can load much appreciable amount of fatty acid molecules into the polymer domain resulting a substantial increased boundary modifier population at the domain-pore interfaces. These PBCM fatty acid molecules, migrated from the polymer bulk phase to the pore interface, can be stabilized even more with anionic dissociation and by forming a charged double layer, especially with the presence of cations other than hydronium ions. This charge double layer is utilized to enhance the partition of cationic drugs and retain them to prolong their release. (FIG. 3).

The present invention provides a method for preparing a nanocomposite comprising hydrophilic polymer domains, hydrophobic polymer domains, water pores, and boundary charged double layers. The method comprises the steps of: (a) soaking a starting nanocomposite comprising hydrophilic polymer domains, hydrophobic polymer domains, and water pores in a solution comprising a proper amount of a boundary charge modifier dissolved in a good solvent that swells either the hydrophilic polymer, or the hydrophobic polymer, and (b) carrying the boundary charge modifiers into the hydrophilic polymer domains or the hydrophobic polymer domains by a swelling process. The method optionally comprises the following steps after soaking: (c) removing the excess solution from the surface of the nanocomposite, and (d) drying the nanocomposite. As an example, the hydrophobic polymer is silicone, and the good solvent is ethanol. As an example, the starting nanocomposite may be a commercial contact lens including those shown in Table 1C, The present invention also provides a method for preparing a nanocomposite comprising hydrophilic polymer domains, water pores, and boundary charged double layers, The method comprises the steps of: (a) soaking a starting nanocomposite comprising hydrophilic polymer domains and water pores in a solution comprising a proper amount of a boundary charge modifier dissolved in a good solvent that swells the hydrophilic polymer, and (b) carrying the boundary charge modifiers into the hydrophilic polymer domains by a swelling process. The method optionally comprises the following steps after soaking: (c) removing the excess solution from the surface of the nanocomposite, and (d) drying the nanocomposite. As an example, the hydrophilic polymer is HEMA and the good solvent is methanol or a mixture of water and ethanol. As an example, the starting n.a.nocomposite may be a commercial contact lens including those shown in Table 1C.

The soaking step of the above two methods is carried out for a proper period of time at a proper temperature. For example, the soaking is from 4 hours to 2 days, or 8-24 hours, or 16-24 hours at 10-40° C., or 20-30° C., or at room temperature.

The following examples further illustrate the present invention. These examples are is intended merely to be illustrative of the present invention and are not to be construed as being limiting.

EXAMPLES

All contact lenses used in the below experiments, including the comparison with J&J clinical trial data, are commercial lenses sourced from Vision Direct BV (York Business Park, YO26 6RB, United Kingdom).

Example 1

Oleic Acid Loading in Commercial Silicone Hydrogel Contact Lenses

Two commercial silicone hydrogel contact lenses were tested: ACUVUE TruEye® (46% Water+54% Narafilcon A)

and ACUVUE Oasys® (38% Water+62% Senofilcon A). TruEye® is a daily disposable contact lens while Oasys® is an approved contact lens for extended wear. The lenses were rinsed with deionized water and then air-dried before being soaked in 4 mL of 19 mg/mL, 27 mg/mL or 40 mg/mL of oleic acid in ethanol. The soaking duration was 24 hours at room temperature. Following the loading step, the contact lenses were taken out and excess fatty acid-ethanol solution was blotted out from the lens surface. Lenses were washed in deionized water for 1 hour and subsequently air-dried overnight.

Figure 4:
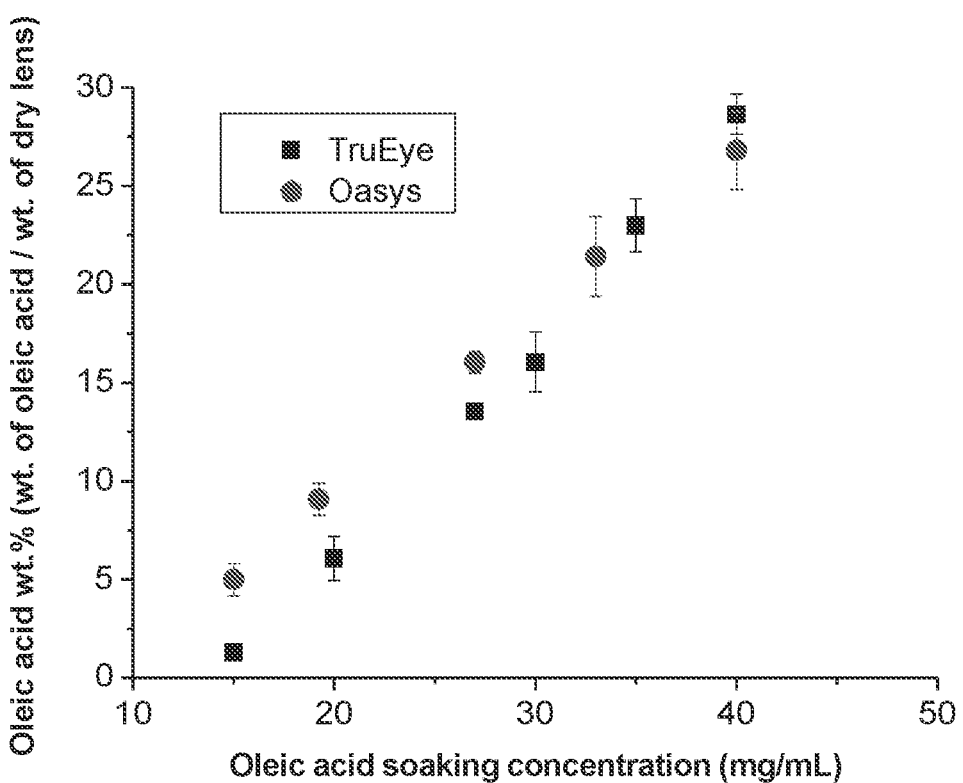

The loading amount of OA was determined by weighing the dry lens before and after the fatty acid loading period as shown in FIG. 4. Oleic acid loading has a linear dependency on the concentration of the loading solutions. Furthermore, Oasys® has higher affinity for oleic acid than TruEye® at concentrations between 15 and 27 mg/mL. For higher concentrations, the affinity for oleic acid is equivalent for both contact lenses. Therefore, the loading of Oleic acid into lens can be adjusted by this correlation.

Example 2

Drug Loading Into Pristine Lenses

Drugs were loaded by soaking the lenses in drug-PBS solution. The soaking duration of the pure lenses was at room temperature and for 24 hours. Following the loading period, the lenses were taken out and excess drug solution on the surface was removed by blotting with filter paper.

Example 3

Figures 5, 6:
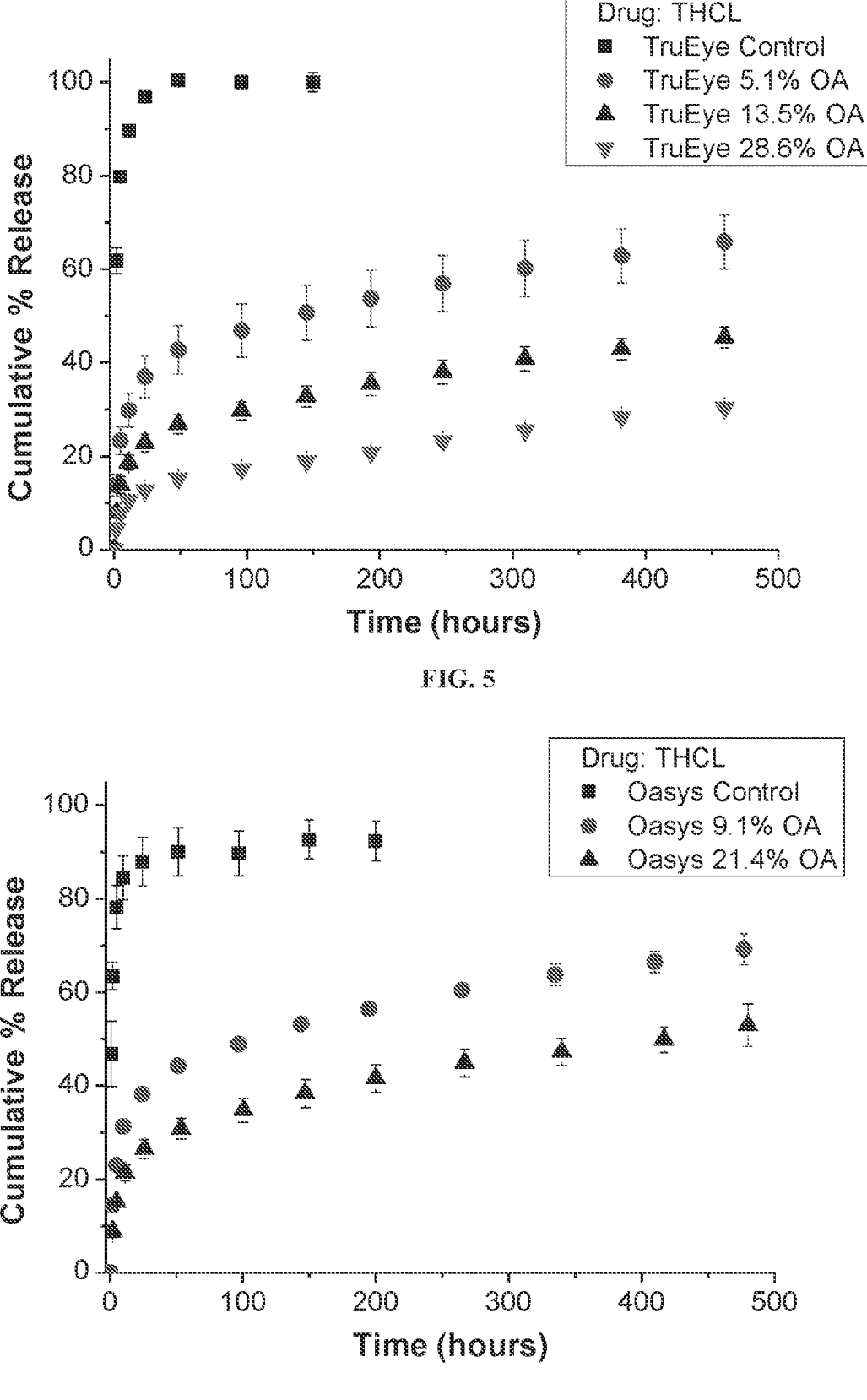
FIG. 5. Cumulative % release of THCL from contact lenses loaded with oleic acid. TruEye® contact lenses.
FIG. 6. Cumulative % release of THCL from contact lenses loaded with oleic acid. Oasys® contact lenses.

Release Kinetics of Cationic Drug Tetracaine Hydrochloride (THCL) from Silicone Hydrogel Contact Lenses Loaded with Oleic Acid FIGS. 5 and 6 show the drug release of THCL from Oasys® and TrulEye® commercial lenses. The cumulative % release of drug is calculated by dividing the amount of drug released at a defined time by the total amount of drug loaded for each lens. From FIG. 5, TruEye® control contact lenses release 80% of THCl in less than 5 hours and approximately 100% in less than 1 day. After 100 hours of release period, TruEye® with 5.1% OA, 13.5% OA, and 28.6% OA release approximately only 47%, 30% and 17% of THCl respectively.

For Oasys® lenses (FIG. 6), control lenses release 100% of THCl in less than 1 day as in the case of TruEye®. 1,enses loaded with 9.1% OA release 49% of THCl, while Oasys® 21.4% OA release 35% after 100 hours. At 400 hours of release period, these percentages increase from 49% to 62% for Oasys® 9.1% OA, and from 35? to 47% for Oasys® 21.4% OA. The presence of oleic acid in both TruEye® and Oasys® contact lenses significantly reduces the drug's burst release and extends the release kinetics of THCL. Furthermore, the presence of oleic acid has a greater effect on extending release kinetics in TruEye® than in Oasys®.

Example 4

Figure 7:
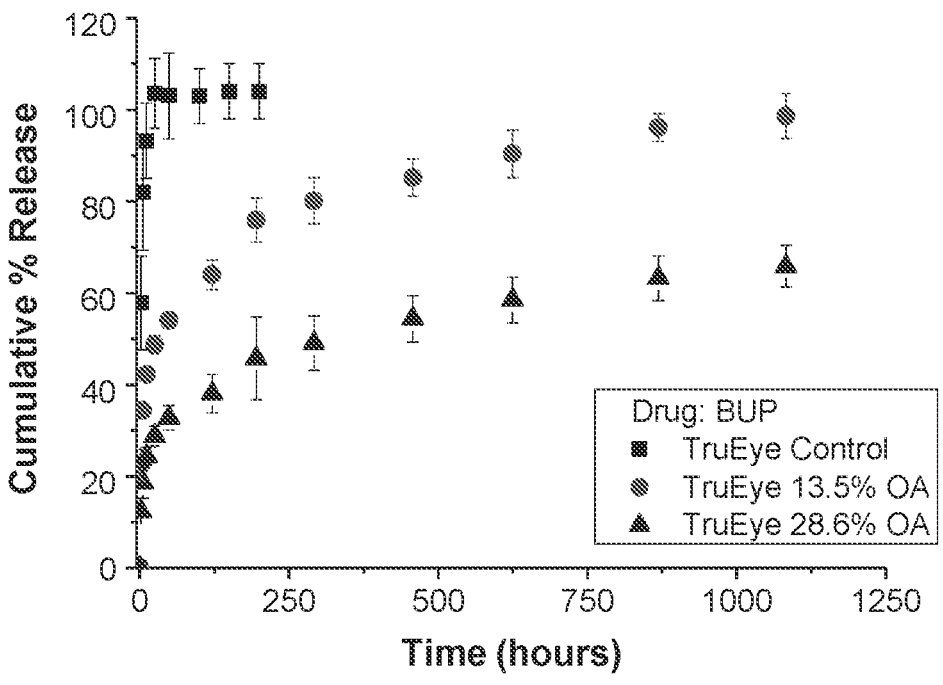
FIG. 7. Cumulative % release of BUP from contact lenses loaded with oleic acid. TruEye® contact lenses.
Figure 8:
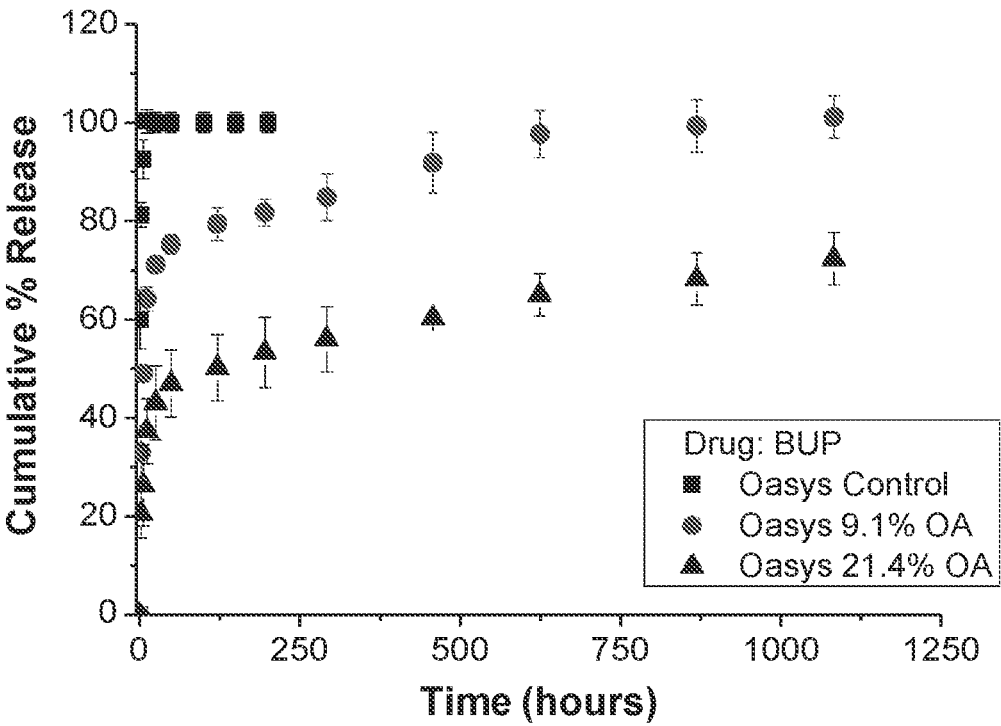
FIG. 8, Cumulative % release of BUP from contact lenses loaded with oleic acid. Oasys® contact lenses.

Release Kinetics of Cationic Drug Bupivacaine Hydrochloride (BUP) from Silicone Hydrogel Contact Lenses Loaded with Oleic Acid FIGS. 7 and 8 show the release kinetics of an anesthetic drug, BLIP from TruEye® and Oasys®. TruEye® control lenses release 80% of loaded KIP in approximately 5 hours. For TruEye® loaded with oleic acid, TruEye® 13.5% OA lenses release 80% of BUP in 300 hours. Based on the release duration for 80% BUP release, the presence of oleic acid in TruEye® can extend the delivery of BUP by a factor of 60-fold. For TruEye® with 28.6% OA, the lenses have only released approximately 60% of loaded BUP after 450 hours. For the case of Oasys®, control lenses release 80% of loaded BUP in approximately 2 hours. Oasys® lenses with 9.1% OA release 80% of BUP in 100 hours. This indicates that oleic acid can prolong the release of BUP by a factor of 50-fold in Oasys® lenses. For Oasys® with 21.4% OA, approximately 75% of loaded BUP is released after 450 hours.

Example 5

Figure 9:
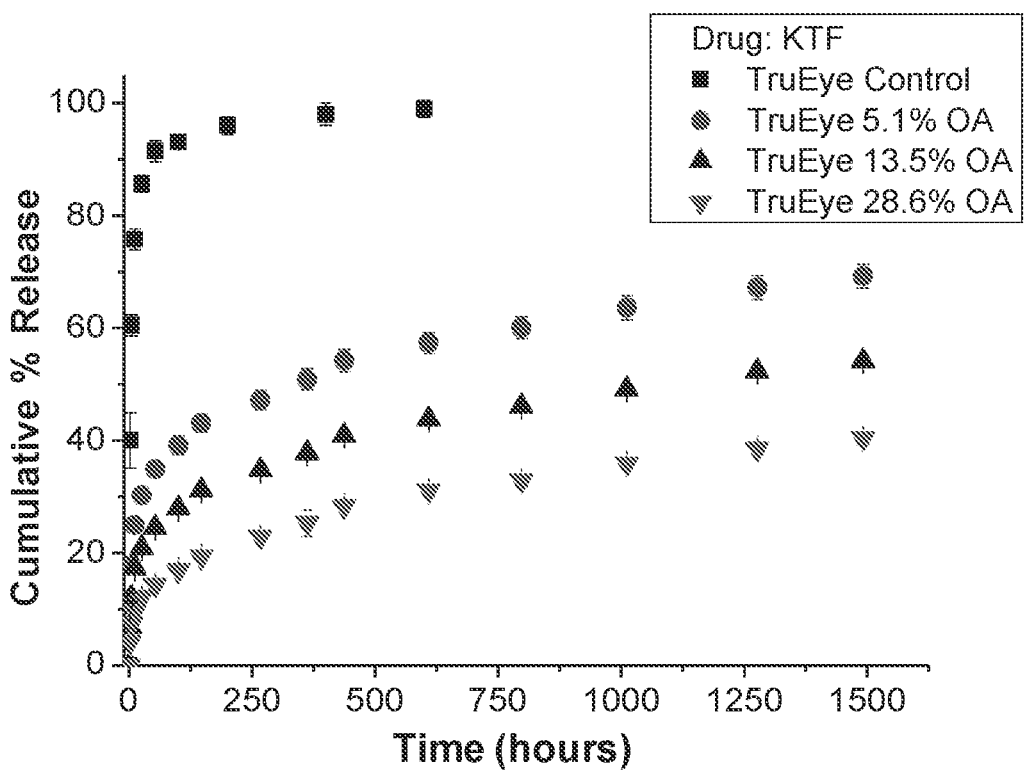
FIG. 9. Cumulative % release of KTF from contact lenses loaded with oleic acid. TruEye® contact lenses.
Figure 10:
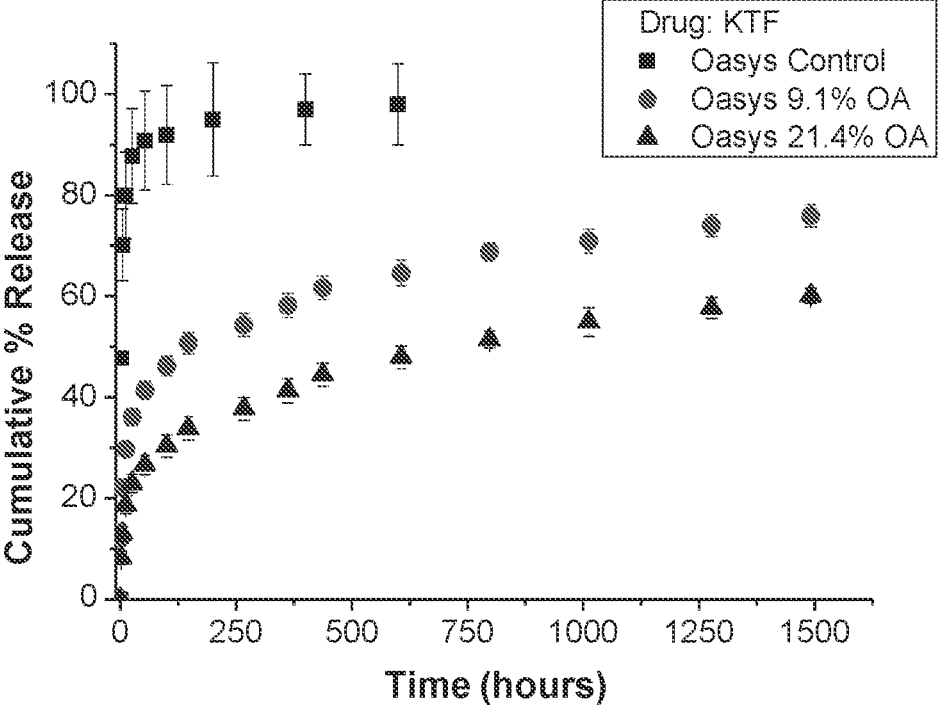
FIG. 10. Cumulative % release of KTF from contact lenses loaded with oleic acid. Oasys® contact lenses.

Release Kinetics of Cationic Drug Ketotifen Fumarate (KTF) from Silicone Hydrogel Contact Lenses Loaded with Oleic Acid FIGS. 9 and 10 show the effect of oleic acid on the release kinetics of KTF, a to relatively selective, noncompetitive antagonist of the histamine H1 receptor. TruEye® control lenses release 80% of loaded KTF in less than 50 hours. TruEye® loaded with oleic acid releases only 40%, 30%, and 18% of loaded KTF after 100 hours for TruEye® 5.1% OA, TruEye® 13.5% OA, and TruEye® 28.6% OA, respectively. For Oasys®, control lenses also release more than 90% of loaded KTF in less than 50 hours, as with the case of TruEye®. After 100 hours, Oasys® 9.1% OA and Oasys® 21.4% OA have released 45% and 30% of loaded KTF, respectively. For both TruEye® and Oasys®, release kinetics are still extended after 1500 hours. Furthermore, the effect of oleic acid is more pronounced with TruEye® than Oasys® lenses.

Example 6

Oleic Acid (OA) Loading into Conventional Hydrogel pHEMA Contact Lenses 1-day ACUVUE Moist® (58% Water+42% Etafi Icon A) are conventional hydrogel commercial lenses that are mostly composed of poly-2-hydroxyethyl methacrylate (pHEMA). Lenses were rinsed with PBS and then air-dried before use. Dry lenses were soaked in 4 mL of 100 mg/mL of oleic acid in a mixture of ethanol and deionized water (75/25 ethanol/ water). Due to the negligible swelling of conventional hydrogel lenses in ethanol, it was decided to soak the lenses in a mixture of ethanol and deionized water since the lenses swell significantly in deionized water. Following the loading step, the contact lenses were taken out and excess fatty acid-ethanol solution was blotted out from the lens surface. Lenses were washed in PBS for 1 hour and then were air-dried overnight. The loading amount of OA was determined by weighing the dry lens before and after the fatty acid loading period.

We found a maximum oleic acid loading of 2.9 wt. %, For instance, when the oleic acid soaking concentration was increased from 100 to 500 mg/mL, the oleic acid loading in 1-day ACUVUE Moist® lenses remained at 2.9 wt. %.

Example 7

Figure 11:
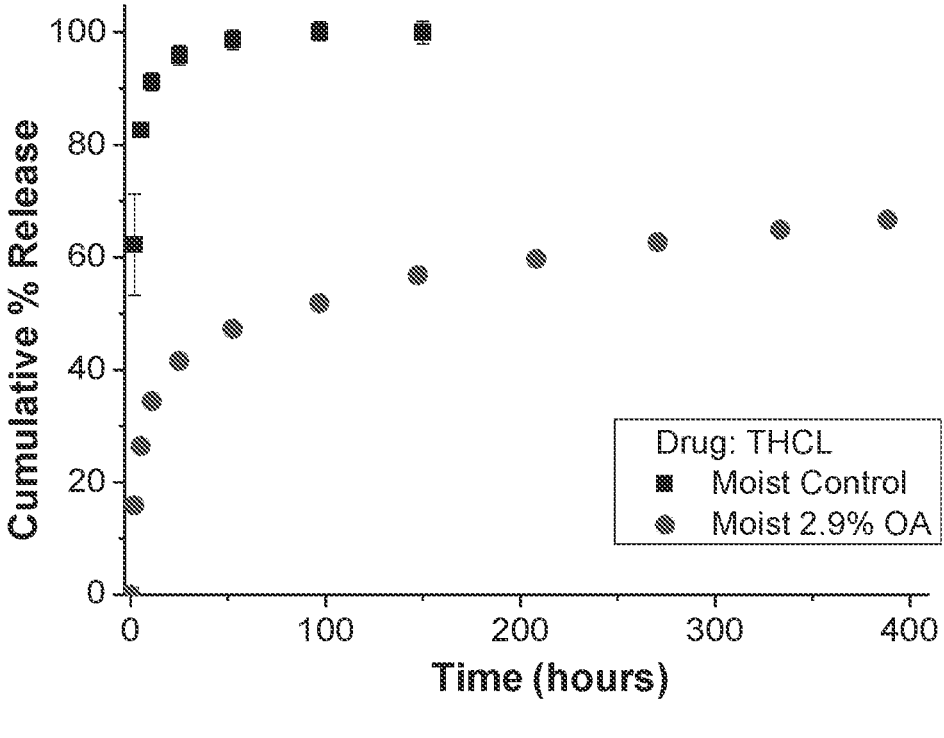
FIG. 11. Cumulative % release of THCL from contact lenses loaded with oleic acid. 1-day ACUVUE Moist® contact lenses.
Figure 12:
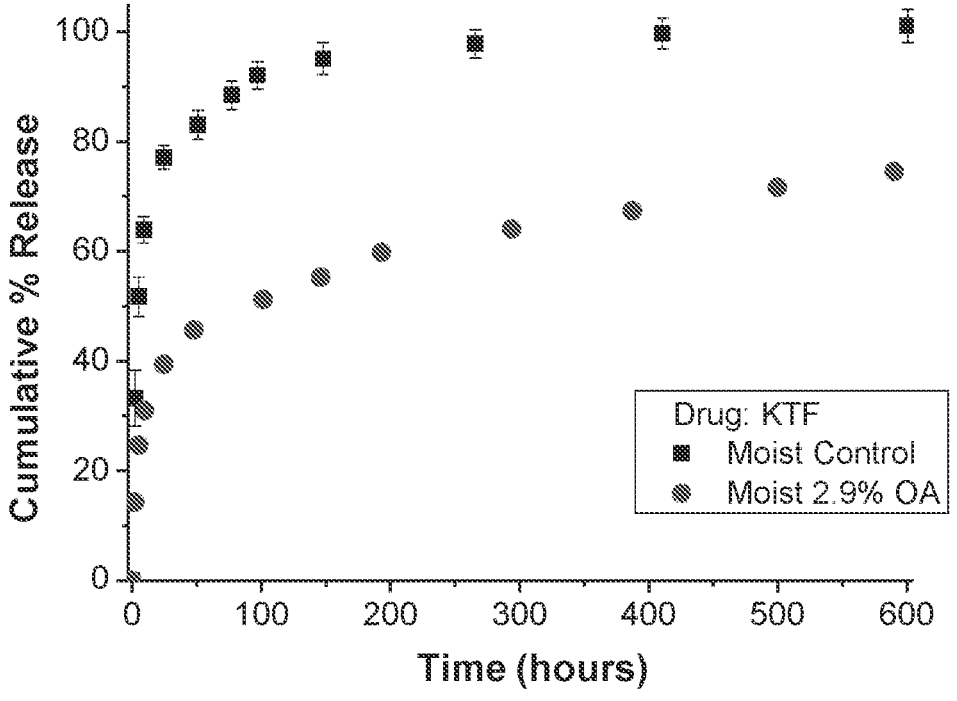
FIG. 12. Cumulative % release of KTF from contact lenses loaded with oleic acid. 1-day ACUVUE Moist® contact lenses.

Release Kinetics of Cationic Drug Tetracaine Hydrochloride (THCL) from 1-Day ACUVUE Moist® Contact Lenses Loaded with Oleic Acid A maximum oleic acid loading of 2.9 wt % was observed for 1-day ACUVUE Moist® contact lenses. Conventional hydrogel contact lenses such as 1-day ACUVUE Moist® do not consist of a hydrophobic region and are predominantly composed of pHEMA hydrophilic polymer. As a result, these lenses have higher water content than silicone hydrogel contact lenses and the lack of hydrophobic silicone domains reduces oxygen permeability and absorption of hydrophobic molecules such as oleic acid. FIGS. 11 & 12 describes the effect of oleic acid in the release kinetics of KTF and THCL from 1-day ACUVUE Moist® contact lenses. Control lenses release 90% of THCL in less than 24 hours. For lenses loaded with 2.9% OA, 60% of THCL is released after 250 hours. For KTF (FIG. 11), control lenses release 80% of drug in approximately 48 hours. For the case of lenses loaded with 2.9% OA, 70% of KTF is released after 500 hours. Therefore, even though the amount of oleic acid loaded in the lenses is limited to 2.9 wt %, the release extension achieved for THCL and KTF is still significant. It should be noted that due to the inability of the lenses to uptake a higher amount of oleic acid, we believe that the drug release extension achieved at 2.9% OA might be the maximum extension that could be achieved for 1-day ACUVUE Moist® contact lenses with the oleic acid loadings.

Example 8

Figure 13:
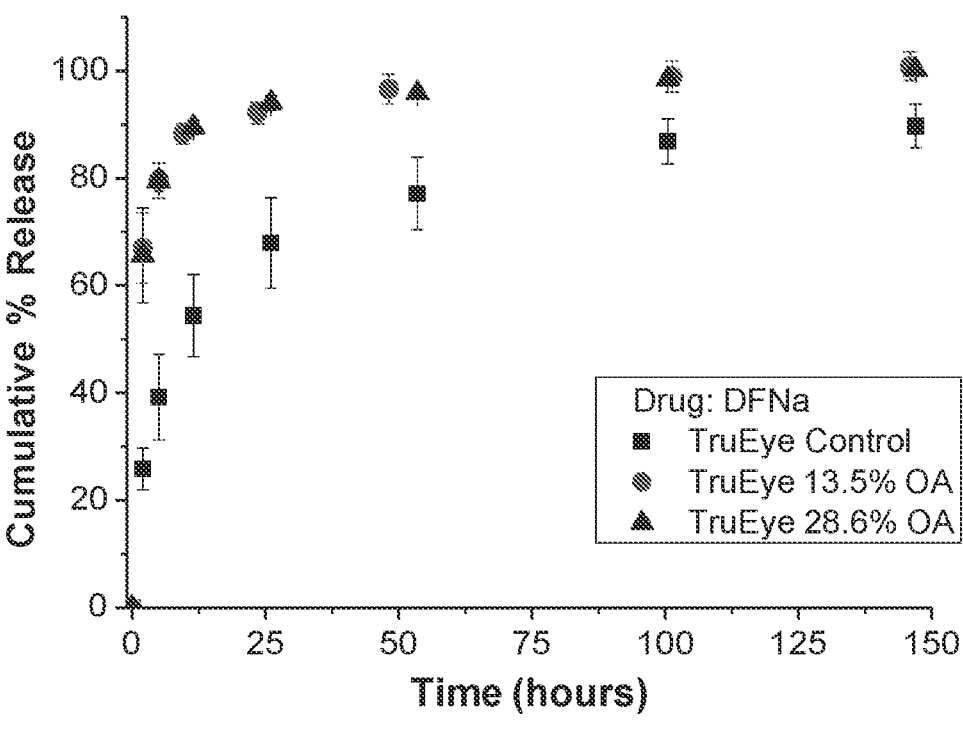
FIG. 13. Cumulative % release of DFNa from contact lenses loaded with oleic acid. TruEye® contact lenses.
Figure 14:
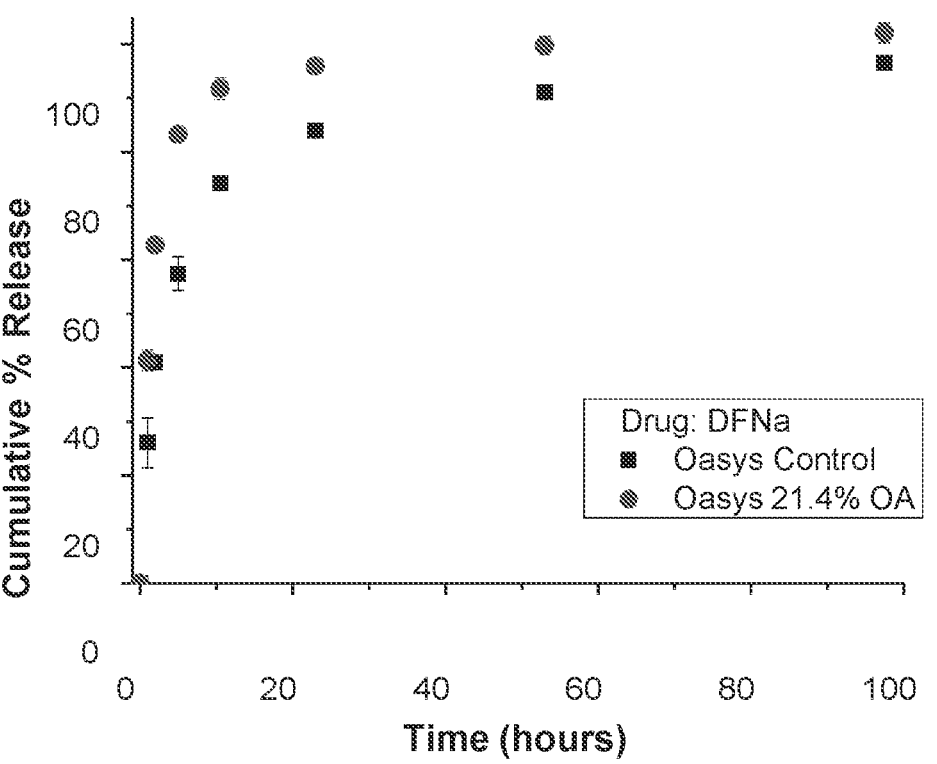
FIG. 14. Cumulative % release of DFNa from contact lenses loaded with oleic acid. Oasys® contact lenses.

Release Kinetics of Anionic Drugs Diclofenac Sodium (DFNa) from Silicone Hydrogel Contact Lenses Loaded with Oleic Acid Diclofenac sodium is one of non-steroidal anti-inflammatory drugs (NSAIDs) that are negatively charged at physiological pH. FIGS. 13 and 14 show the effect of oleic acid on the release of DFNa from TruEye® and Oasys® contact lenses. TruEye® lenses (FIG. 12) with 13.5% and 28.6% OA release 80% of DFNa in approximately 5 hours, while TruEye® control lenses release 80% in 60 hours. For Oasys® (FIG. 14), lenses with oleic acid release 80% DFNa in 4 hours, while control lenses release 80% of DFNa. in 20 hours. Therefore, DFNa is released faster from contact lenses loaded with oleic acid than from lenses without oleic acid. Based on the times for 80% drug release, DFNa. is released 12 times faster from TruEye® lenses loaded with oleic acid compared to the control lenses. For Oasys®, DFNa is released 5 times faster from lenses with oleic acid than from control lenses.

Example 9

Figure 15:
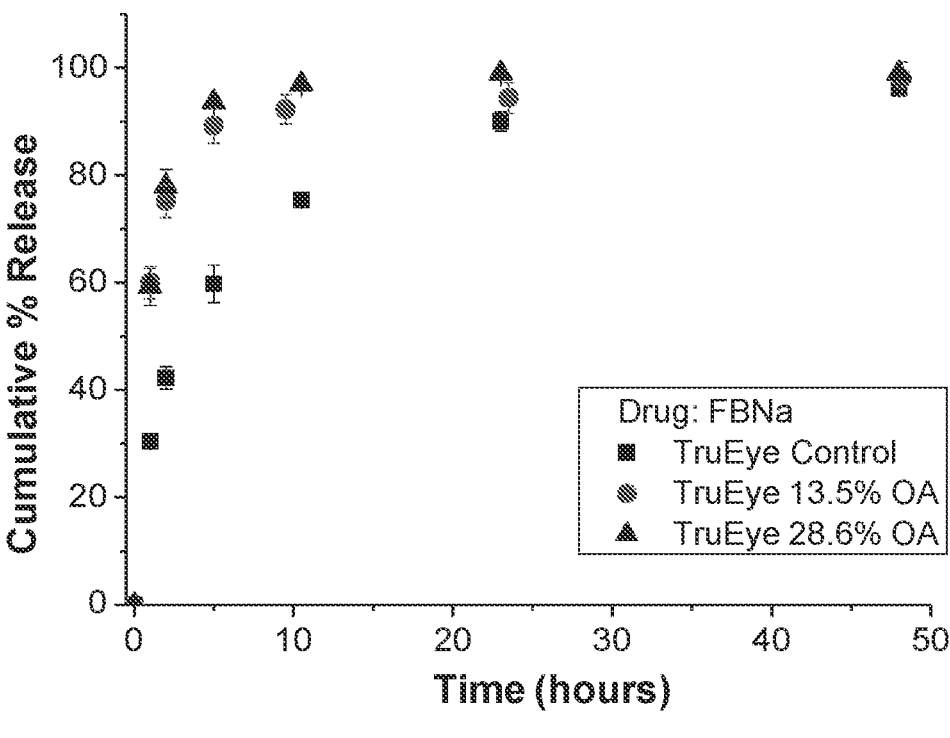
FIG. 15. Cumulative % release of FBNa from contact lenses loaded with oleic acid. TruEye® contact lenses.
Figure 16:
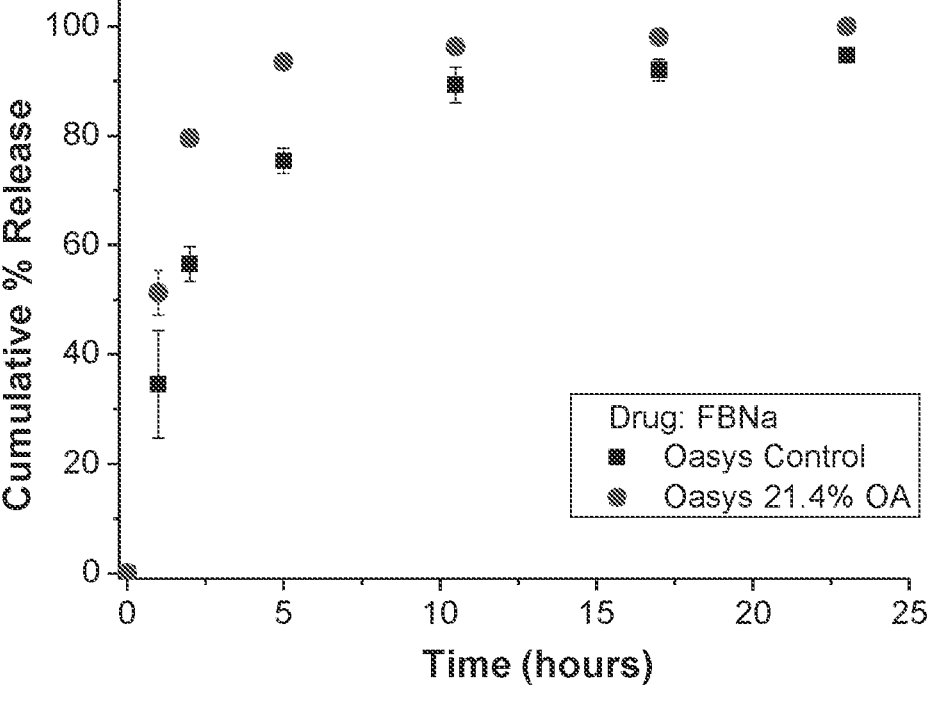
FIG. 16. Cumulative % release FBNa from contact lenses loaded with oleic acid. Oasys® contact lenses.

Release Kinetics of Anionic Drug Flurbiprofen Sodium (FBNa) from Silicone Hydrogel Contact Lenses Loaded with Oleic Acid Flurbiprofen sodium (FBNa) is a nonsteroidal anti-inflammatory drug for postoperative cataract surgery. FIGS. 15 and 16 show the effect of oleic acid on FBNa release. In FIG. 15, TruEye® lenses with 13.5% and 28.6% OA release 80% of FBNa in 2 hours, while control lenses release 80% in 12 hours. For the case of Oasys®, lenses loaded with oleic acid release 80% of FBNa in 2 hours, while control lenses release 80% in 6 hours. As with the case of DFNa, FBNa is being released faster from contact lenses loaded with oleic acid. Based on the times for 80% drug release, FBNa is released 6 and 3 times faster compared to the controls for TruEye® and Oasys® loaded with oleic acid, respectively.

From the results obtained for DFNa and FBNa, it can be concluded that the presence of anionic oleic acid in silicone hydrogel contact lenses accelerates the drug release of anionic drugs due to repulsive ionic interactions. Furthermore, it was evidenced that the effect of oleic acid on accelerating the release kinetics of DFNa and FBNa is more its pronounced for TruEyet than for Oasys®.

Example 10

Comparison of Release Kinetics of KTF from ACUVUE TruEye® Contact Lenses Loaded with Three Different Fatty Acids—Oleic Acid, Linoleic Acid, or α-Linolenic Acid Oleic acid is a long-chain unsaturated fatty acid with one double bond. Linoleic acid and α-linolenic acid are unsaturated fatty acids with the same number of carbons as oleic acid, but with two and three double bonds, respectively. These three fatty acids are oily liquids at room temperature. However, due to the different number of double bonds, we hypothesize that their packing density at the hydrophobic domain's aqueous interface might affect the drug release kinetics.

Figure 17:
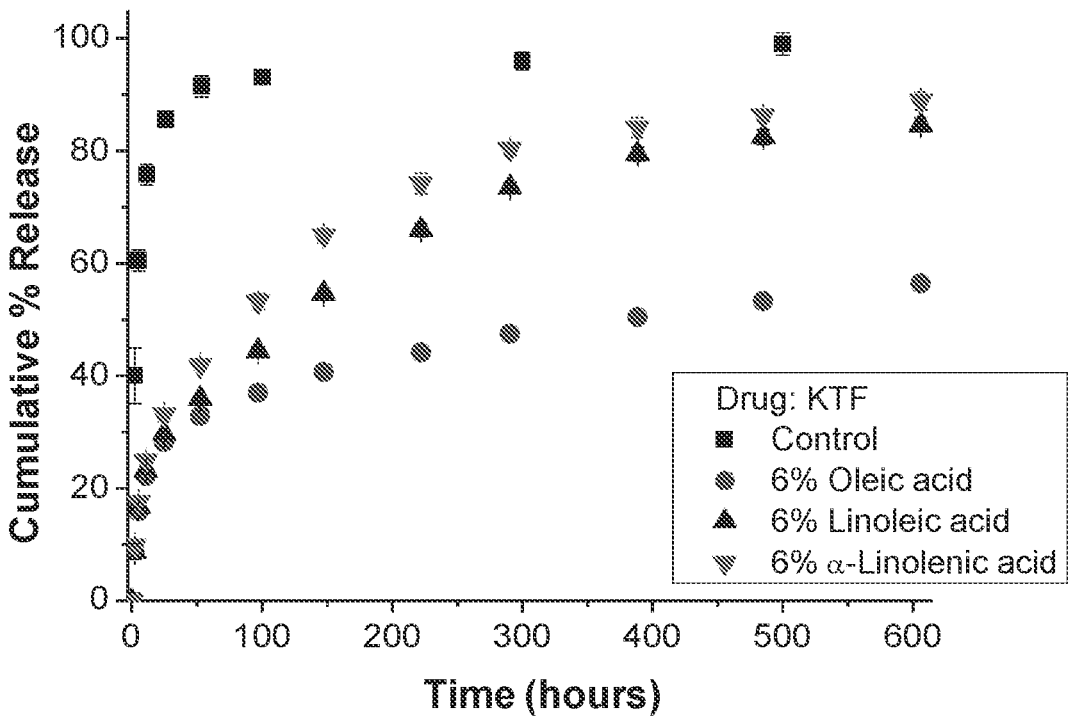
FIG. 17. Cumulative release of KTF from ACUVUE TruEye® contact lenses loaded with 6% wt. of oleic acid, linoleic acid, or α-linolenic acid.

We tested a soaking concentration of 20 mg/mL of fatty acid in ethanol in ACUVUE TruEye® contact lenses as summarized in FIG. 17. At the same fatty acid soaking concentration, fatty acid loading was found to be similar, i.e. 6.1 wt % for oleic acid, 6.2 wt % for linoleic acid, and 6.0 wt % for α-linolenic acid. From FIGS. 17, 37%, 44% and 53% of KTF is released after 100 hours of release period for oleic, linoleic, and α-linolenic acid, respectively. Interestingly, the difference of the release kinetics becomes more significant among the three fatty acids after 200 hours of release petiod. The increasing number of cis double bonds does kink and bend the chain more to compromise its packing in a monolayer at the interface. The difference in the charge density at the aqueous interfaces among the three fatty acids can explain the difference in the KTF release kinetics, with oleic acid achieving the most extended release. Nevertheless, all fatty acid loaded lenses significantly prolong KTF as compared with the control.

Example 11

Release Kinetics of Anionic Drugs (DFNa) from Silicone Hydrogel Contact Lenses Loaded with Sphingosine ACUVUE TruEye® commercial lenses were rinsed with deionized water and then air-dried before use. ACUVUE TruEye® contact lenses were soaked in 4 mL of 6.5 mg,/mL sphingosine in ethanol. The soaking duration was 24 hours at room temperature. Following the loading step, the contact lenses were taken out and excess sphingosine-ethanol solution was blotted out from the lens surface. Lenses were washed in deionized water for 1 hour and subsequently air-dried overnight.

Diclofenac sodium was loaded by soaking the lenses in 5 mL of a 0.2 mg/mL drug-PBS solution. The soaking duration of the pure lenses was at room temperature and for 24 hours. Following the loading period, the lenses were taken out and excess drug solution on is the surface was removed by blotting with filter paper. To determine the amount of drug loaded in each lens, the drug concentration of each soaking solution was measured before and after the soaking period using a UV-visible spectrophotometer (Varian Cary 50 Bio, Walnut Creek, CA, USA). After the drug loading step, lenses were tested using in vitro release experiments.

Figure 18:
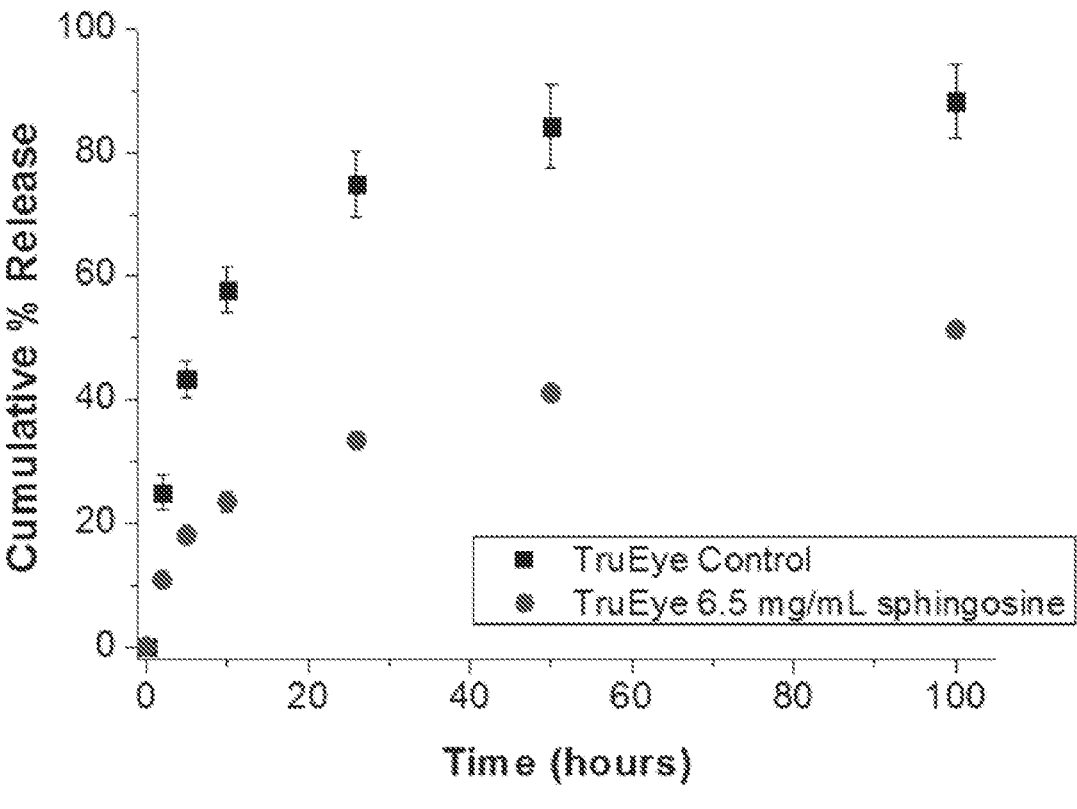
FIG. 18. Cumulative % release of DFNa from contact lenses loaded with 6.5 mg/mL Sphingosine TruEye® contact lenses.

FIG. 18 shows the effect of Sphingosine on DFNa el ease. in FIG. 18, TruEyet lenses with 6.5 mg/mL Sphingosine loading solution release only 40% of DFNa in 100 hours, while control lenses release 80% in 12 hours. Sphingosine also increases DFNa uptake from 187.1±16.1 µg; in control lens to 590.0±0.7 µg.

Example 12

Comparison of Release Kinetics of Ketotifen Fumarate from ACUVUE TruEye® Contact Lenses Loaded with Two Different Saturated Fatty Acids—Myristic Acid (Tetradecanoic Acid) and Stearic Acid (Octadecanoic Acid)

ACUVUE TruEye® (diopter −3.5) contact lenses were rinsed with deionized. water and then air-dried overnight before use. One batch of contact lenses were soaked in 4 mL of 7.5 mg,/mL of myristic acid in ethanol. Another batch of contact lens were soaked in 4 mL of 7.5 mg/mL of stearic acid in ethanol. A third batch of lenses was used as a control (no fatty acid loading). The soaking duration was 24 hours at 23° C. Following the loading step, the contact lenses were taken out and excess fatty acid-ethanol solution was blotted out from the lens surface. Lenses were washed in deionized water for 1 hour and subsequently air-dried overnight. All contact lenses were optically transparent in the hydrated state. The wt % of fatty add retain by the contact lens was determined by recording the increase in the weight of the dried lens after the soaking and drying procedure. For both stearic and myristic acid, approximately 1.5% ±0.5% by weight of the dried lens was composed of the fatty acid.

Ketotifen fumarate (KTF) was loaded by soaking the lenses in 5 mL of a 0.3 mg/mL KTF in PBS solution. Following the loading period (24 hours at 23° C.), the lenses were taken out and excess drug solution on the surface was removed by blotting with filter paper. To determine the amount of KTF loaded in each lens, the KTF concentration of each soaking solution was measured before and after the soaking period using a UV-visible spectrophotometer (Varian Cary 50 Bio, Walnut Creek, CA, USA). After the drug loading step, lenses were tested using in vitro release experiments. The drug release experiments were carried out by soaking the drug loaded lenses in 3 mL of Dulbecco PBS at pH 7.4 and at 23° C. During the release experiments, I ml, of release sample was removed at predetermined time intervals, and 1 mL of fresh PBS was refilled into the release medium. The amount of drug released was measured using a UV-Spectrophotometer (Varian Cary 50 Bio) at wavelengths of 300 nm. The drug release experiments were performed in triplicate for each different case. It was thus determined the control lenses uptake was 176 pg of KTF, while lenses loaded stearic acid gave a slightly increased uptake of 214 pg. In comparison, the contact lenses with myristic acid showed significantly improved uptake of 516 µg of KTF.

Figure 19:
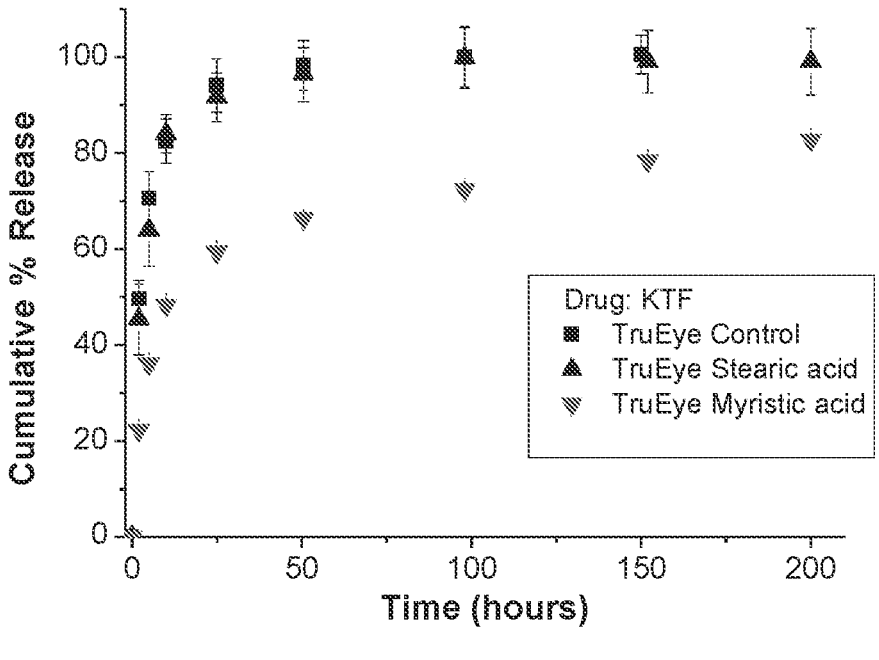
FIG. 19. Cumulative % Release of KTF from ACUVUE TruEye® silicone hydrogel commercial lenses. Fatty acids in contact lenses were loaded at a fixed soaking concentration of 7.5 mg/mL. 176.3 µg±18.6 µg for TruEye® Control, 214.3 μg±38.7 μg for TruEye® 7.5 mg/mL stearic acid, 516.4 μg +4.2 μs for TruEye® 7.5 mg/mL myristic acid, FIG. 20. Linear correlation of Ketotifen uptake (in a range of 70-375 μg /CL KTF load) with solution loading concentration.

FIG. 19 shows the effect of the stearic and myristic acid on the release kinetics of KTF from ACUVUE TruEye® contact lenses. Here we define the term "release duration" as the time for 70% cumulative drug release. The control lenses (no fatty acid) have a release duration of 5 hours, whilst lenses loaded with stearic acid and myristic acid have release duration of 6 hours and 60 hours respectively. A release duration between 8 and 24 hours is consistent with the daily wear schedule of the lenses.

Example 13

Oleic Acid (OA) Loading into Pristine Silicone Hydrogel Contact Lenses

In this example, the medical device is a commercial silicone hydrogel, ACUVUE Oasys® contact lens (Johnson & Johnson Vision Care, Inc., Jacksonville, Fla.) and the fatty acid PBCM is oleic acid. This lens consists HEMA hydrophilic polymer, silicone hydrophobic polymer and has 38% water content in aqueous pores. Ethanol is a good solvent that can swell the silicone phase. The silicone hydrogel commercial lenses were rinsed with &ionized. water and then air-dried before use. ACUVUE Oasys® contact lenses were soaked in 4 mL of 19 mg/mL or 33 mg/mL of oleic acid in ethanol. ACUVUE TruEye® contact lenses were soaked in 4 mL of 19 mg/mL, 27 mg/mL or 40 mg/mL of oleic acid in ethanol. The soaking duration was 24 hours at room temperature. Following the loading step, the contact lenses were taken out and excess fatty acid-ethanol solution was blotted out from the lens surface, and the lens was air-dried overnight. The loading amount of OA was determined by weighing the dry lens before and after the fatty acid loading period.

Example 14

Oleic Acid (OA) Loading into Pristine Conventional Hydrogel pHEMA Contact Lenses In this example, the medical device is a HEMA 1-day ACUVUE Moist® contact lens to and the fatty acid. PBCM is oleic acid. One-day ACUVUE Moist® are conventional hydrogel commercial lenses that are mostly composed of poly-2-hydroxyethyl methacrylate (pHEMA), which is hydrophilic, but more hydrophobic than the aqueous pores (water content is 58%). Ethanol does not swell HEMA lens, but methanol is a good solvent that can swell the HEMA phase. Lenses were rinsed with PBS and air-dried overnight before use. Dry lenses were soaked in 4 mL of 100-300 mg/mL oleic acid in methanol. The soaking duration was maintained at 24 hours and at room temperature. After soaking, excess fatty acid-methanol solution was blotted out from the lens surface, and lens was immersed in PBS for 1 hour for washing remaining methanol left, Following washing, lenses were left to dry overnight.

Example 15

Oleic Acid (OA) Loading into Pristine Conventional Hydrogel pHEMA Contact Lenses In this example, the medical device is a HEMA 1-day ACUVUE Moist® contact lens and the fatty acid PBCM is oleic acid. Methanol is a good solvent for swelling but not good for processing because minor residual could be harmful to the eyes. Due to the negligible swelling of conventional hydrogel lenses in ethanol, we alternatively developed a water/ethanol solvent mixture that can swell the HEMA phase. Lenses were rinsed with PBS and then air-dried before use. Dry lenses were soaked in 4 mL of 100 mg/mL of oleic acid in a mixture of ethanol and deionized water (75/25 ethanol/water). Following the loading step, the contact lenses were taken out and excess fatty acid-ethanol solution was blotted out from the lens surface. Lenses were washed in PBS for 1 hour and then were air-dried overnight.

The loading amount of OA was determined by weighing the dry lens before and after the fatty acid loading period.

Example 16

High-Precision Control of KTF Delivery Dosage and Timing

This example demonstrates the high-precision of oleic acid boundary charge control technique. We first confirmed that the total KTF loading in oleic acid loaded lens can be precisely determined by drug concentration in a solution loading process.

Figure 20:
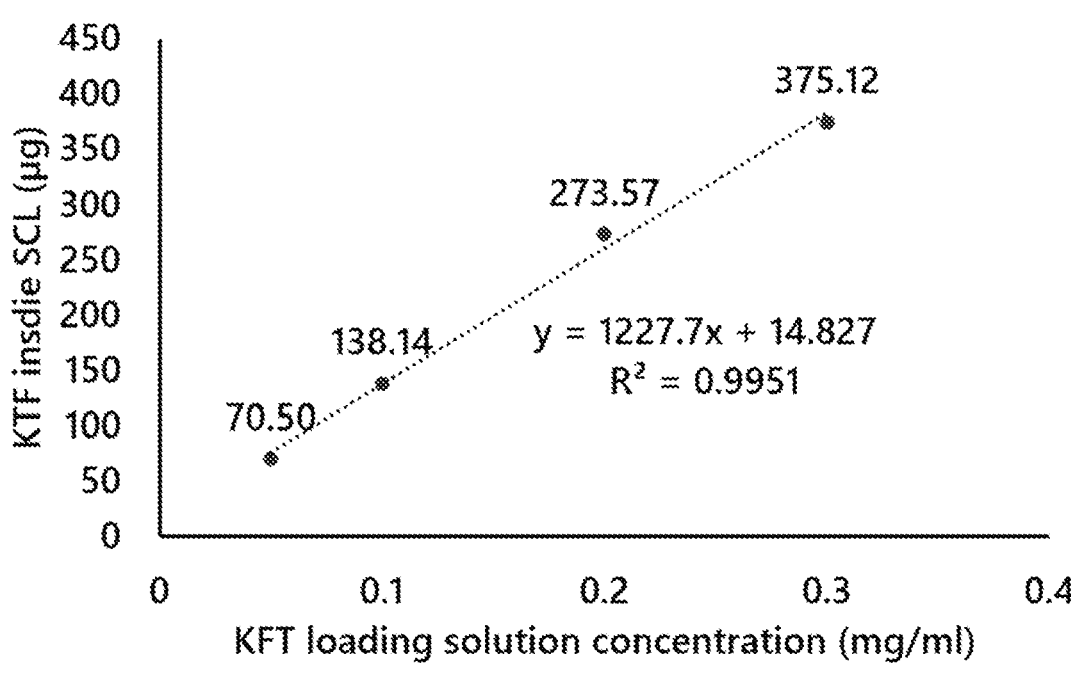

The lens brand was ACUVUE TruEye and oleic acid 2-4% (calculated from dry lens weight change which may fluctuate with drying conditions) were loaded by the same ethanol soaking process with 15 mg/mL oleic acid in ethanol as described in Example 1. KTF is loaded according to procedures in Example 2. FIG. 20 showed a linear correlation in KTF loading range of 70-375 µg/CL to the solution loading concentration, Furthermore, we verified that, with a fixed amount of oleic acid loading (oleic acid, loading condition is 15 mg/ml in ethanol), the kinetic release profile is the same over such a wide range of 70-375 µg/CL KTF loading per contact lens (FIG. 21).

Our data in Example 10 also manifested the easy extension of the same KTF release profile to more than 600 hours with the adjustment of oleic acid loading to 6% (FIG. 17) and further to 1500 hours with increasing oleic acid loading to 9.1 (Example 5, FIG. 10), By studying the optimal loading combination of oleic acid and KTF drug %, it is expected that we can make a silicone-hydrogel lens that precisely delivers 80% of KTF payload at a low average dosage within exactly one week.

Figure 21:
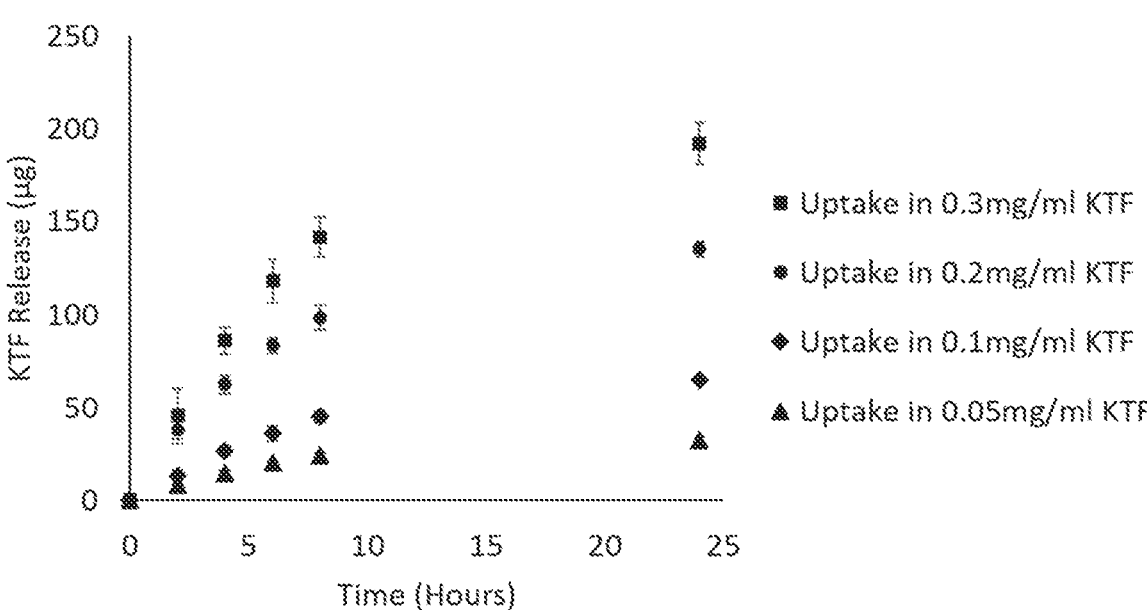
FIG. 21. The consistent delivery kinetic profile in relation to a broad range (70-375 μg/CL) of Ketotifen loaded and released from a 2% oleic acid (loading condition oleic acid 15 mg/ml ethanol) loaded contact lens.

According to the consistency trend shown in FIGS. 20 and 21 regarding the dependencies of cumulative percentage release rate to the amount of oleic acid loading in the CL across a broad range, it is expected that we can prescribe a precise recipe of drug and oleic acid loading weight in a commercial contact lens to deliver over 80% of embedded amount of KTF (for example, 80 µg) within a desired duration (for example, 5 days), thus accomplish the high-precision drug delivery control.

Johnson & Johnson's ACUVUE Theravision is the first approved product (Japan) for delivering a drug Ketotifen (KTF) from a daily disposable hydrogel lens. Ex vivo results from J&J etafilcon A-KTF releasing contact lens showed that nearly 90% of drug is released in less than 2 hours (see FIG. 1, column 1, line 58, U.S. Pat. No. 9,962,376). By comparing the results of Examples 6, 10, and 16 with J&J clinical trial data disclosed in U.S. Pat. No. 9,962,376 Patent as described above, the oleic acid loaded contact lens of the present invention can (a) more precisely control the daily delivery dosage of KTF in a broad range of 1-375 microgram, (b) extend this precise dosage delivery duration from a few hours to several weeks (600 hours), substantially longer than the burst release of J&J clinical data shown in U.S. Pat. No. 9,962,376 Patent, (c) achieve the same precisely controlled KTF delivery from both HEMA daily disposable hydrogel lens (see Example 6), which is the only type of lens in J&J clinical trial, as well as the more versatile longer-term wearing silicone-hydrogel lens (see Examples 10 and 16).

The invention, and the manner and process of making and using it, are now described in such full, clear, concise and exact terms as to enable any person skilled in the art to which it pertains, to make and use the same. It is to be understood that the foregoing describes preferred. embodiments of the present invention and that modifications may be made therein without departing from the scope of the present invention as set forth in the claims. To particularly point out and distinctly claim the subject matter regarded as invention, the following claims conclude the specification.

What is claimed is:

1. A medical device comprising a nanocomposite and a drug, wherein the nanocomposite comprises hydrophilic polymer domains, hydrophobic polymer domains, water pores, and boundary charged double layers; wherein when the drug is hydrophilic, at least 80% of the drug partitions in the boundary charged double layers formed at the boundary interface of the hydrophilic polymer domains and water pores, and when the drug is hydrophobic, at least 80% of the drug partitions in the boundary charged double layers formed at the boundary interface of the hydrophobic polymer domains and water pores.

2. A medical device comprising a nanocomposite and a drug, wherein the nanocomposite comprises hydrophilic polymer domains, water pores, and boundary charged double layers, and at least 80% of the drug partitions in the boundary charged double layers formed at the boundary interface of the hydrophilic polymer domains and water pores.

3. The medical device according to claim 1 or 2, wherein each of the boundary charged double layers comprises (i) the charge of a head group of a boundary charge modifier, and (ii) the charge of the drug or a counter ion to the charged head group, wherein the boundary charge modifier is a molecule having a charged head group and a hydrophobic tail and is immobilized at the boundary charged double layer throughout the life of the device.

4. The medical device according to claim 1 or 2, wherein the hydrophilic polymer is formed from a monomer with logP <1, wherein the monomer comprises one or more hydrophilic groups selected from the group consisting of: a hydroxy group, an alkyl glycol, an amine, a lactam, a carboxylic group, and a sulfonic group.

5. The medical device according to claim 4, wherein the monomer is 2-hydroxyethyl methacrylate ("HEMA"), N,N-dimethylacrylamide ("DMA"), N-vinyl-2-pyrrolidone ("NVP"), 4,4-dimethyl-2-vinyl-2-oxazolin-5-one, methacrylic acid ("MAA"), N-(hydroxymethyl)acrylamide, N-[3-(dimethylamino)propyl]methacrylamide, or ethylene glycol dimethacrylate.

6. The medical device according to claim 1, wherein the hydrophobic domain comprises a hydrophobic polymer formed from a monomer or an oligomer with a logP >3, wherein the monomer comprises one or more hydrophobic groups selected from the group consisting of: an alkyl group, an aromatic group, an ester group, a perfluoroalkyl group.

7. The medical device according to claim 6, wherein the monomer is 3-[tris(trimethylsiloxy)silyl]propyl methacrylate ("TRIS"), 3-methacryloxy-2-hydroxypropoxy (propyl-bis(trimethylsilyloxy) methylsilane ("SIGMA"), dimethyl siloxane, monomethyl siloxane, fluorosiloxane, or methyl Methacrylate (MMA).

8. The medical device according to claim 1, wherein the water pores are about 10 to 40% by weight, and the size of each of the polymer domains is between 10 to 100 nanometers.

9. The medical device according to claim 3, wherein the boundary charged modifier is a fatty acid with a carbon chain length of 8-24 and one carboxylic acid head, and the drug is positively charged.

10. The medical device according to claim 9, wherein the boundary charged modifier is oleic acid, linoleic acid, a-linolenic acid, myristic acid, or stearic acid.

11. The medical device according to claim 3, wherein the boundary charged modifier is an alkyl amine, or ethanolamine with a carbon chain length of 8-24 and one amine or ethanolamine head group, and the drug is negatively charged.

12. The medical device according to claim 11, wherein the boundary charged modifier is sphingosine.

13. The medical device according to claim 1, which is a contact lens, surgically implanted body part, a stent, a chemo port, a scaffold for tissue growth, a tooth implant, a skin pad, or a wound-healing bandage.

14. A method for preparing a nanocomposite comprising hydrophilic polymer domains, hydrophobic polymer domains, water pores, and boundary charged double layers, comprises the steps of:

soaking a starting nanocomposite comprising hydrophilic polymer domains, hydrophobic polymer domains, and water pores in a solution comprising a boundary charge modifier dissolved in a good solvent that swells either the hydrophilic polymer, or the hydrophobic polymer, and carrying the boundary charge modifiers into the hydrophilic polymer domains or the hydrophobic polymer domains by a swelling process.

15. A method for preparing a nanocomposite comprising hydrophilic polymer domains, water pores, and boundary charged double layers, comprises the steps of:

soaking a starting nanocomposite comprising hydrophilic polymer domains and water pores in a solution comprising a boundary charge modifier dissolved in a good solvent that swells the hydrophilic polymer, and carrying the boundary charge modifiers into the hydrophilic polymer domains by a swelling process.

16. The method according to claim 14, wherein the hydrophobic polymer is silicone and the good solvent is ethanol.

17. The method according to claim 14 or 15, wherein the hydrophilic polymer is HEMA and the good solvent is methanol.

18. The method according to claim 14 or 15, wherein the hydrophilic polymer is HEMA and the good solvent is a mixture of water and ethanol.

19. The medical device according to claim 10, wherein the boundary charged modifier is oleic acid, linoleic acid, a-linolenic acid, or myristic acid.

* * * * *